United States Patent [19]

Wieder

[11] 4,150,295
[45] Apr. 17, 1979

[54] METHOD AND APPARATUS FOR BACKGROUND CORRECTION IN PHOTOLUMINESCENT ANALYSIS

[75] Inventor: Irwin Wieder, Los Altos, Calif.

[73] Assignee: Analytical Radiation Corporation, Los Altos, Calif.

[21] Appl. No.: 867,004

[22] Filed: Jan. 5, 1978

[51] Int. Cl.² .............................................. F21K 2/02
[52] U.S. Cl. ................................... 250/458; 250/354; 250/461 B
[58] Field of Search ................... 250/458, 459, 461 R, 250/461 B, 214 C, 354

[56] References Cited

U.S. PATENT DOCUMENTS

| | | | |
|---|---|---|---|
| 3,891,853 | 6/1975 | Kremen et al. | 250/461 B X |
| 3,967,113 | 6/1976 | Soodak et al. | 250/214 C |
| 4,006,360 | 2/1977 | Mueller | 250/461 B |
| 4,045,679 | 8/1977 | Wolfe et al. | 250/461 R X |
| 4,058,732 | 11/1977 | Wieder | 250/461 B |

Primary Examiner—Davis L. Willis
Attorney, Agent, or Firm—Thomas Schneck, Jr.

[57] ABSTRACT

A method and apparatus for background correction in photoluminescent analysis of a selected photoluminescent target substance with a relatively narrow emission spectrum in the presence of ambient substances with a combined photoluminescent spectrum which is relatively broad. The photoluminescence of the target substance is sampled and measured in a narrow wavelength band corresponding to the principal emission spectrum of the target. A second sample of photoluminescence is measured in one or more wavelength bands adjacent to the first wavelength band, but excluding substantially all of the photoluminescence of the target substance, and transmitting only ambient photoluminescence. The second measurement is converted into an amount which would occur if ambient photoluminescence had been sampled in the first wavelength band and then the converted amount is subtracted from the first measured amount, thereby correcting the first measured amount for photoluminescence derived from ambient substances.

7 Claims, 6 Drawing Figures

METHOD AND APPARATUS FOR BACKGROUND CORRECTION IN PHOTOLUMINESCENT ANALYSIS

BACKGROUND OF THE INVENTION

1. Field of the Invention

The invention relates to photoluminescent analysis and more particularly to a method and apparatus for determining and correcting for background luminescence in measurements of the amount of luminescent target material.

2. Prior Art

Many substances found in nature are naturally photoluminescent, especially those of organic origin. Thus, quantitative photoluminescent methods are plagued with the problem of ambient photoluminescence interfering with measurements of low concentrations of photoluminescent target substances. It is true that some benefits can be gained by preferentially exciting photoluminescence at the optimum wavelengths for target excitation and observing photoluminescence at the optimum wavelengths for target emission. However, this technique is somewhat limited as the concentration of target molecules is decreased. This is because, for most substances, excitation bandwidths and photoluminescent emission bandwidths are very broad, typically 500 A° and broader, and furthermore there are usually many ambient substances with excitation and emission overlap with target molecules. Because of the superposition of the excitation and emission spectra of many species, the spectrum of the entire ambient sea of substances is usually much broader than 500 A°.

This problem has to some extent been solved in U.S. Pat. No. 4,058,732, wherein a target is tagged with a photoluminescent tag with photoluminescent lifetime long compared with ambient photoluminescent substances, and a detection system is gated on only after photoluminescence from ambient substances has decayed. Using that system in combination with rare earth chelates, the range of photoluminescent detectability of rare earths in the presence of background substances has been extended by orders of magnitude.

At this new level of detectability the limiting factor is ambient photoluminescence which is long lived in comparison with ambient fluorescence. At such decay times where the fluorescence of ambient substances has certainly decayed some very weak phosphorescence and "delayed fluorescence" remains. Now, phosphorescence and delayed fluorescence are phenomena which are mostly quenched in liquid systems at room temperature. Nevertheless, at extremely low target concentrations, say $10^{-9}$ or $10^{-10}$ g/cc, ambient luminescent substances which may be of much higher concentrations can give competitive long lived luminescent signals even though they are substantially quenched. See Parker, Photoluminescence in Solutions, Elsevier, 1968, for discussions of residual long lived photoluminescence in solutions. Another source of weak long lived background signals is the phosphorescence of the solid matrix of the sample support or container. These two sources of long lived photoluminescence are the factors which are presently preventing the attainment of further sensitivity.

The benefits of increased sensitivity can be projected to be of importance whether considering the detectability limits on a pure fluorophore or a target tagged with a fluorophore. In the former case, improved sensitivity would be of value in the method of using dyes as tracers to measure the flow of fluids. In that technique a fixed amount of dye is put into the fluid at one point, and the concentration of dye measured downstream at later times. This enables a calculation of the rate that fluid moves in the system. By improving the sensitivity of fluorophore detection, one conserves the amount of dye needed for the measurement. In the case of targets tagged with a fluorophore, clinical tests for substances in bodily fluids are becoming more widely used in medical diagnosis, and the demands for increased sensitivity are following the need to determine substances which are present in smaller quantities. In both of these examples, there are background substances which limit the sensitivity of fluorometric measurement of a fluorescent target.

In dealing with the interference from background substances, it is sometimes possible to determine the background signal in the absence of the fluorophore. Where the test procedure allows this, prior art techniques have been established in which a reading is taken in the appropriate wavelength range of the system minus the fluorophore and then again with the fluorophore, and the first reading is subtracted from the second to obtain the true reading due to the fluorophore. However, there are cases where it is impossible or inconvenient to use this prior art subtraction technique. For example, in the case of fluid flow measurement mentioned above, samples without fluorophores may be long distances away from the point of measurement, and background may be different at these distant points. Or in the clinical test lab, reagents which are added to bodily fluids as part of the test procedure may produce some background photoluminescence in themselves, or may affect the level of other background fluorescence which was present prior to their addition. Thus, a method which could determine the level of background signals in the presence of the fluorophore and test reagents is desirable.

Accordingly, it is an object of the present invention to correct for ambient photoluminescent signals in the wavelength and time domain, and in the presence of fluorescent target substances and associated reagents, in order to extend the limits of fluorescent detectability in the presence of ambient substances beyond their present limits.

SUMMARY OF THE INVENTION

The above object is achieved in a background correction method and apparatus wherein a photoluminescent target substance is selected to be either a fluorophore or a substance labeled with a fluorophore such that the fluorophore has a sharp photoluminescent spectrum in comparison with the broad emission spectrum which typifies the emission of background or ambient substances. A sample of photoluminescence from the target is defined by the collected photoluminescence which is transmitted by a filter or through a monochromator in a first narrow wavelength band centered at the peak of the principal emission wavelength of the target substance. This first sample is measured, and the measurement includes the photoluminescence of both the target and ambient species, with the photoluminescence resulting from an excitation source, such as a laser.

A second sample of photoluminescence is taken in one or more narrow wavelength bands which are proximate to, but substantially outside of the first band such that photoluminescence of the target is excluded from this sample, but background photoluminescence is included. The photoluminescence of the second sample results from the same excitation energy as that of the first sample. The second sample is measured and the measurement is converted to an amount due to ambient photoluminescence present in the first wavelength band, assuming that broad band photoluminescence due to ambient substances changes only slightly in the narrow wavelength region defined by the two sampling procedures. The converted amount is then subtracted from the first measured amount thereby leaving an amount of photoluminescence due to the target substance alone.

An advantage of the invention is that background photoluminescence which combines with the photoluminescence of the target substance may be subtracted without the necessity of removing the target from the measuring apparatus. Moreover, time domain discrimination may be employed with long lived fluorophores such that the decay of a large number of organic background materials or other ambient species may occur before making the measurement.

To limit any error in measurements the excitation energy for the targets is stabilized by means of a feedback loop. Moreover, an internal standard is provided in order to compensate for errors associated with detector drift.

DESCRIPTION OF THE PREFERRED EMBODIMENT

In the present invention, we are concerned with the detection of selected targets with relatively sharp photoluminescence spectra in the presence of ambient background. These targets may be sharp spectrum fluorophores in themselves, such as rare earth chelates or substances previously tagged with these fluorophores. These selected targets exist in a sea of photoluminescent ambient background substances. For example, in clinical laboratory applications it is desirable to detect trace amounts of chemical substances at levels of less than nanograms per cubic centimeter in the presence of blood serum. A large class of proteins and other background substances which might be found in blood have fluorescent decay lifetimes of less than 50 nanoseconds. For example, see the article entitled "Fluorescent Decay Times: Proteins, Coenzymes, and Other Compounds in Water", by R. F. Chen, *Science*, May 19, 1967, pp. 949-951 at Table 1, p. 950. Target observation times for long lived fluorophores, beyond the decay lifetimes of these background substances, may be established by time gating of a detection system after the decay of shorter lived background substances. Now however, the background problem turns to weak phosphorescence, "delayed fluorescence" and phosphorescence of the solid matrix of the sample support or container.

Figure 1A:
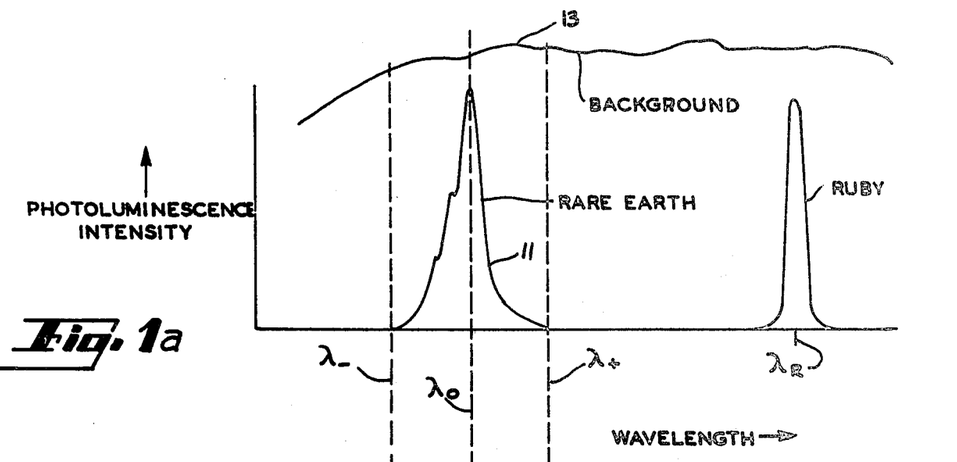
FIGS. 1a, 1b and 1c show a typical rate earth fluorescence wavelength spectrum compared with typical background photoluminescence and the transmission windows of the signal filter and background filter.

The spectrum of a preferred fluorophore, a rare earth chelate in solution, to be used as a target or label for a target, is shown by curve 11 in FIG. 1a. The emission spectrum is usually in the range of about 100 A° full width at half height or less at room temperature and decreases markedly at lower temperatures. By comparison, typical background photoluminescence is shown by curve 13 to be much broader and a relatively slowly varying function in the wavelength range of the rare earth fluorescence. As mentioned above, this is because background photoluminescence is inherently much broader and furthermore is a result of the superposition of photoluminescence from many species. Rare earth chelates are not the only type of fluorophores which may be used. In general, the target must be a photoluminescent substance selected from the group consisting of certain fluorophores and substances labelled with these fluorophores. Such fluorophores must have a sharp photoluminescent emission spectrum in comparison with the combined broad emission spectrum of ambient substances.

Figure 1B:
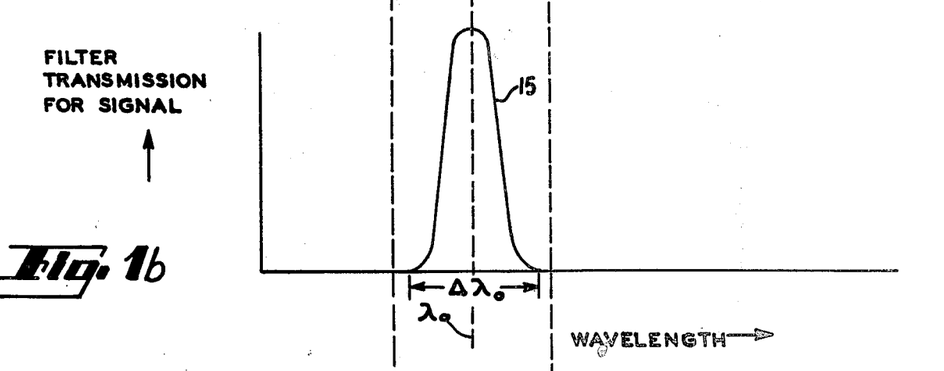
Figure 1C:
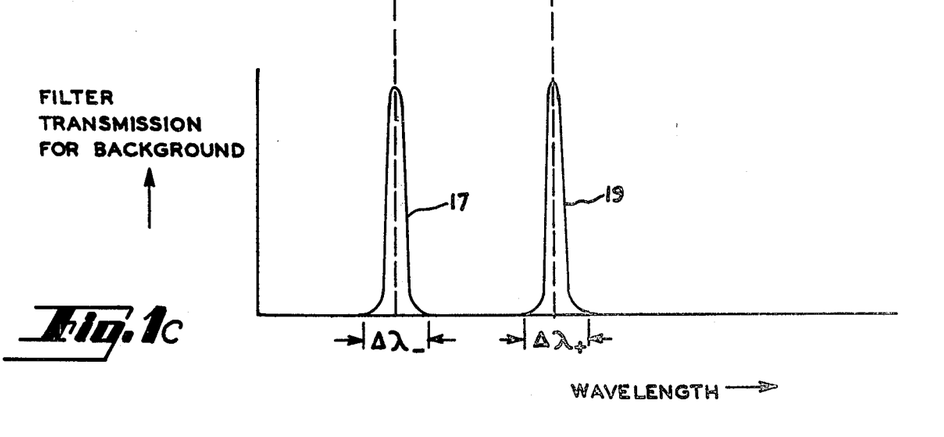

According to the present invention, a correction is made for ambient photoluminescence in the presence of a fluorescent target and in the same bandwidth and time domain of the detection system for target fluorescence. The photodetection system for target fluorescence includes a narrow band interference filter or monochromator or the like centered at a wavelength of $\lambda_o$, the peak of rate earth target fluorescence, to accept and transmit the target fluorescence and reject the background which is outside the bandwidth of an interference filter. The term filter will be used to describe a class of transmission means which may be used to sample photoluminescence of the fluorophore and background. FIG. 1b shows the filter transmission characteristic curve 15 which accepts most of the rare earth fluorescence, curve 11 of FIG. 1a, and rejects much of the background photoluminescence, curve 13 of FIG. 1a. Nevertheless, an amount of background photoluminescence corresponding to the region $\Delta\lambda_o$ on the background curve in FIG. 1a interferes with the measurement of target fluorescence. The filter characterized by the transmission curve 15 in FIG. 1b samples an amount of photoluminescence in the first selected narrow wavelength band which is centered at $\lambda_o$, the peak of the principal emission wavelength of the target illustrated in FIG. 1c. That amount of photoluminescence is comprised of both target and ambient photoluminescence which are derived from a common amount of excitation energy from a source, such as a pulsed laser. The filter is said to sample the photoluminescence of target plus background because only a fraction of the total photoluminescence is incident on the filter and its transmission curve does not transmit all of that fraction, only an amount falling within its wavelength dependent transmission characteristic. Narrow bandwidth interference filters for this purpose are well known.

In the present invention, the level of background in a wavelength range $\Delta\lambda_o$ around the principal emission wavelength $\lambda_o$ of the fluorophore is approximated by monitoring the background in the wavelength bands $\Delta\lambda_-$ and $\Delta\lambda_+$ around wavelengths $\lambda_-$ and $\lambda_+$ respectively. Background photoluminescence is monitored in the two wavelength bands by sampling and measuring an amount of ambient photoluminescence at each wavelength by means of a filter having a transmission characteristic shown by the curves 17, 19 in FIG. 1c. Measurement consists of operations performed on photocurrent from detector 51 in signal processor 71. These operations include measurement of the photocurrent followed by storage in a memory bank. Photoluminescence in at least one of the wavelength bands, $\Delta\lambda_-$ or $\Delta\lambda_+$ must be measured as a minimum. If both wavelengths are measured, an average is taken as described herein. These three wavelength bands, $\Delta\lambda_o$, $\Delta\lambda_-$ and $\Delta\lambda_+$, correspond to three detection bandwidths defined by three interference filter transmission curves, 15, 17, 19, respectively, shown in FIGS. 1b and 1c. Wavelength regions $\Delta\lambda_-$ and $\Delta\lambda_+$ are very close to $\Delta\lambda_o$ and on either side, but not close enough to transmit a significant portion of radiation from the target fluorescence centered at $\lambda_o$, i.e., less than 1%–2% of the target fluorescence that is transmitted by the filter in the $\Delta\lambda_o$ range.

The filter whose transmission peak is centered at $\lambda_o$ is typically chosen to allow the bulk of the radiation from the target, i.e., at least 90% or more to fall within the bandwidth $\Delta\lambda_o$ and to have a peak transmission "T" as high as possible. The actual choice of bandwidth is a compromise between the desirability of transmitting as much target fluorescence as is practical and the desirability of transmitting as little background luminescence as possible, and may vary depending on the extent of background present.

Figure 2:
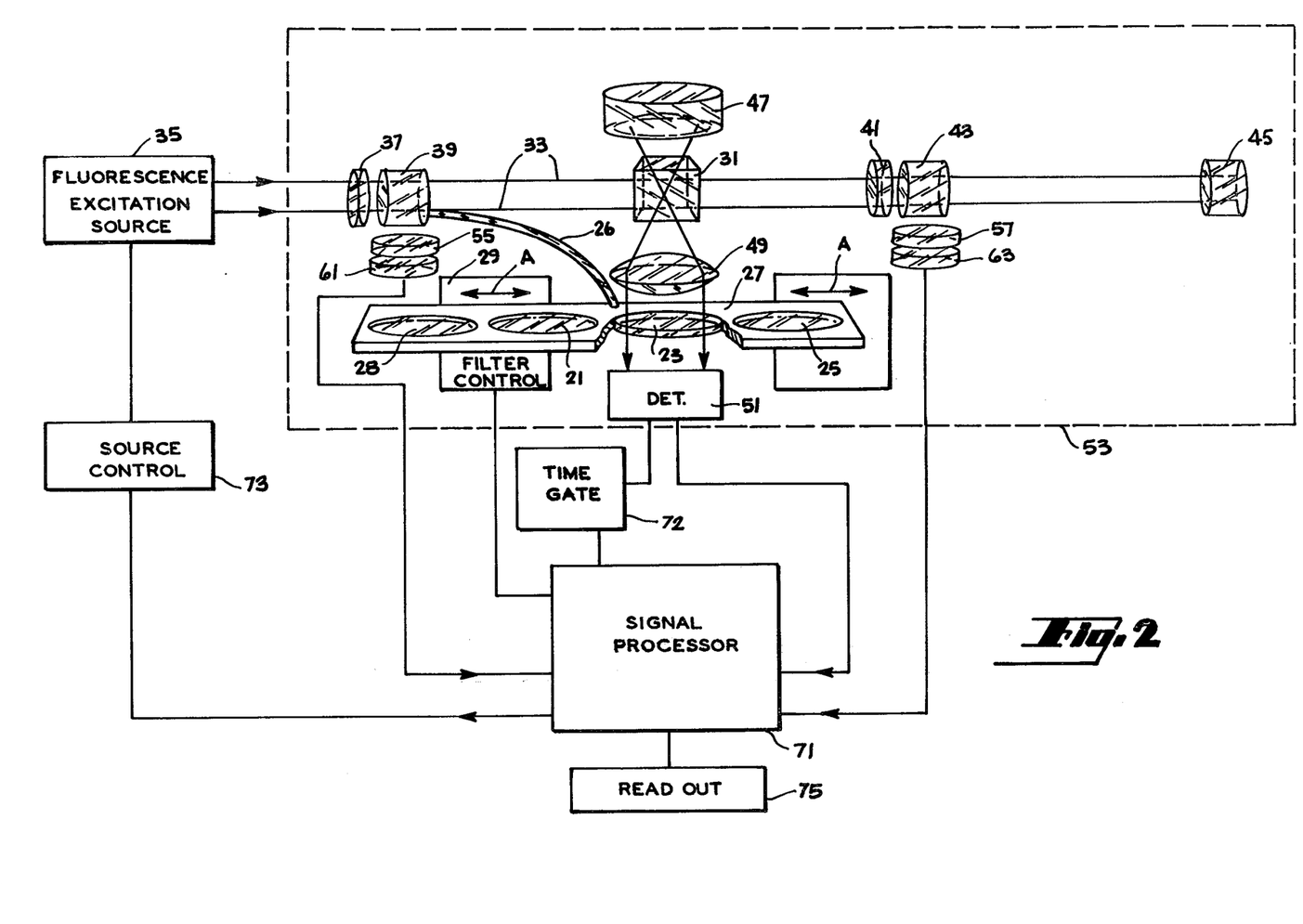
FIG. 2 is a schematic diagram of a fluorometer of the present invention.

The arrangement of the various filters in a fluorometer may be viewed with reference to FIG. 2. In FIG. 2, the filters 21, 23, 25, 28 are shown to be held in a holder 27 which is movable by means of filter control 29 in the direction indicated by the arrows A. A target substance is placed in a sample holder 31 and illuminated by excitation carried by beam 33 generated by a continuous fluorescence excitation source 35 which may be a laser. An excitation filter 37 removes undesired wavelength components from the beam before the beam passes through ruby cylinder 39 which serves as an internal standard described below. After the beam passes through sample container 31, it is directed into a cleanup filter 41 prior to passing into the second ruby cylinder 43 and thence into a beam terminator 45 which is a light trap, preventing retroreflection of the beam. Photoluminescence from substances in container 31 is collected by concave mirror 47 and lens 49. Concave mirror 47 directs the photoluminescence it collects toward focusing lens 49 which directs collimated light through one of the selected filters 21, 23, 25 or 28 and thence into the photodetector 51 which may be a photomultiplier.

All of the optical components mentioned above, with the exception of the fluorescence excitation source 35, are housed in a light-tight cabinet indicated by the dashed line 53 with an opening to allow entry of the excitation beam. Optical components in cabinet 53 which were not previously mentioned include the ruby filters 55, 57 which transmit fluorescence of the respective rubies 39,43 to photodiodes 61, 63 which are mounted in close proximity to the filters 55, 57. The photodiodes 61, 63 have output signals which are connected to the signal processor 71. Signal processor 71 also receives an input from photodetector 51. Signal processor 71 has two outputs, one being source control 73, an amplifier and switch for controlling the on and off times of excitation source 35 and the second being a readout device 75 which may be a teletypewriter or a digital display.

The signal processor 71 is a mini or micro computer suitable for carrying out the operations described below.

The collection factor for photoluminescence in the enclosure 53 is called "k", where "k" contains all the geometrical factors which determine the fraction of total photoluminescence which is incident on the collection filter 21, 23, 25 or 28. If $I_b$ is the intensity distribution of the unwanted background photoluminescence, then the flux through the filter per unit bandwidth is given by $I_b(\lambda)T(\lambda)Ak$, where A is the area of the collection filter and detector behind it, and $T(\lambda)$ is the filter transmission factor. The photocurrent signal, for filter 23, centered at $\lambda_o$ is:

$$S_o = Ak \int_{\Delta\lambda_o} I_b(\lambda) \, T_o(\lambda) \, D(\lambda) \, d\lambda$$

where $D(\lambda)$ is the sensitivity of the detector as a function of $\lambda$. The photocurrent signals $S_-$ and $S_+$ for filters 21 and 25, respectively are:

$$S_+ = Ak \int_{\Delta\lambda_+} I_b(\lambda) \, T_+(\lambda) \, D(\lambda) \, d\lambda$$

$$S_- = Ak \int_{\Delta\lambda_-} I_b(\lambda) \, T_-(\lambda) \, D(\lambda) \, d\lambda$$

These three integrals executed by processor 71 represent background signals corresponding to the three wavelength regions under consideration.

Now according to the method of the present invention $S_o$ is approximated by a linear combination of $S_-$ and $S_+$ or, $$S_o = aS_+ + bS_-$$

where "a" and "b" are weighting factors which depend on $T(\lambda)$ and $D(\lambda)$ this amounts to a conversion of the measured amount of ambient photoluminescence in the other selected wavelength bands $\Delta\lambda_+$ and $\Delta\lambda_-$ to an amount which would occur from ambient photoluminescence measured in the first selected wavelength band $\Delta\lambda_o$. To account for the wavelength dependence of $T(\lambda)$ and $D(\lambda)$ and determine the values of "a" and "b" to be used for the correction, signals are taken in the presence of typical background, but in the absence of target. This allows for a determination of "a" and "b" for the particular photodetector response, and the particular filters chosen. At least two different backgrounds with different slopes are needed to determine "a" and "b". To the extent that $I_b$ is linear in the wavelength range in question this approximation carried out by processor 71 is accurate.

The correction is applied in the following way: Once "a" and "b" are determined for the system and stored in the memory of the signal processor 71, a sample with an unknown amount of target is inserted and successive readings are taken with the three filters 21, 23, 25 corresponding to $\lambda_-$, $\lambda_o$, and $\lambda_+$, respectively. These readings are performed in sequence on command from the signal processor 71. For example, with filter 21 in place, $S_-$, may be read first, multiplied by weighting factor "b" and stored in the memory; then filter control 29 controlling the position of filters 21, 23, 25 and 28 moves the next filter 23 corresponding to $\lambda_o$ into position, and signal is read. Note that this signal now includes the target fluorescence signal, $S_t$, as well as $S_o$, i.e. $S_t + S_o$. This value is stored and the filter 25 corresponding to $\lambda_+$ is moved into place by filter control 29 and another reading taken. This value is multiplied by weighting factor "a", combined with the value of $bS_-$ and subtracted from the reading taken at $\lambda_o$. These operations, carried out by signal processor 71 correspond to:

$$(S_t+S_o)-(aS_++bS_-)\cong S_t$$

so that a determination of $S_t$ is obtained by this procedure.

The fluorometer excitation source 35 may be a pulsed source such as a nitrogen laser or flash lamp or a continuous source. The use of a pulsed source enables time gating to be applied and enables discrimination against background fluorescence which is short compared with long lived target fluorescence in accordance with the method of U.S. Pat. No. 4,058,732 mentioned above. Pulsed signals are then integrated and the above correction method is applied to the integrated signals.

The trigger pulses for the source are generated within the signal processor 71 and are fed to a source control 73 which amplifies the trigger to a voltage and duration suitable for triggering the source to discharge and emit radiation.

The source output is collimated and directed through a filter 37 and then a transparent cylinder of lightly doped ruby 39 through the sample and container 31 if used and through a second filter 41 and ruby 43 to a beam absorber 45. Fluorescence from ruby 39 in the region $\lambda_R$ is similar to rare earth fluorescence in that it is sharp spectral long lived emission, but is at a different wavelength than the rare earth. Ruby has been found to be a vary stable fluorophore.

Fluoroescence from the first and second rubies 39, 43 may be monitored after passing through filters 55 and 57, respectively, by photodetectors 61 and 63, respectively, such as United Detector Technology PIN photodiodes which are very stable and linear in their response. These two measurements effectively monitor the excitation beam incident on the sample and transmitted by the sample.

The fluorescence from the sample in container 31 is collected by an optical collection system including mirror 47 and lens 49 and collimated so that it is nearly perpendicular to an interference filter 21, 23, or 28, and then measured by a photodetector 51, typically a photomultiplier. Four or more interference filters are placed in a sliding or rotating filter holder 27 which periodically places different interference filters in front of the photodetector in sequence, and on command from the signal processor 71.

Filter 23 is at $\lambda_o$, filter 28 is at the ruby sharp line fluorescence in the vicinity of 6943 A°, $\lambda_R$, filter 21 is at $\lambda_{31}$, and filter 25 is at $\lambda_+$. See FIGS. 1b and 1c.

A small light pipe 26 directs a portion of the fluorescence from the first ruby 39 through the interference filter holder 27 and to the photodetector 51. A measurement of an unknown quantity of target in a sample is accomplished as follows:

At the beginning of a series of determinations of an amount of target material in various samples, the detector 51 is standardized by taking a reading on ruby fluorescence with a preset amount of excitation energy. A first sequence of pulses from the excitation source 35 is initiated with, say, the reference ruby filter 28 in place in front of the detector 51. When the proper integrated excitation energy is reached as determined by photodetector 61, the laser pulses are stopped by source control 73 on command from processor 71 and the signal processor 71 reads and stores information on the integrated, time gated signal at detector 51 from ruby cylinder 39. This value is then used to standardize readings of detector 51 during the day. That procedure may take, say, about 1 sec which would mean about 100 pulses if the source is operating at 100 pps. Thus, the amount of excitation energy used in each sampling process is stabilized by feedback.

For every succeeding sequence of measurements, a reading is always first taken on the ruby 39 to take into account any drift in the detector 51 which is more sensitive than detector 61 but usually not as stable. Drift in detector 51 is compensated in this way. Thus, the fluorometer of the present invention has two further error reduction features, besides the subtraction of an amount of signal representing an estimate of background from the total detected signal plus background. The first is excitation source stabilization, achieved by use of an internal ruby reference in a feedback loop whereby a pulsed excitation source is cut off when the proper excitation energy is reached. The second is signal compensation of the detector by referencing detector signals to prior detector readings of the reference ruby and calibrating the detector to earlier ruby signal levels.

Next a series of standard solutions of target material are measured using the same integrated excitation energy, as determined by detector 61. Filter control 29, a servo, on command from the signal processor 71, moves the different interference filters 21, 23, 25, 28 into position and a sequence of pulses is initiated and stopped when the preset integrated excitation is reached. This is repeated for each filter in the sequence.

Readings for each concentration are obtained for wavelength regions, $\Delta\lambda_-$, $\Delta\lambda_o$, $\Delta\lambda_+$ and corrections to the readings at $\Delta\lambda_o$ are determined. These corrected $\Delta\lambda_o$ readings are then stored in the memory of the signal processor.

The fluorometer is now ready to measure samples containing unknown amounts of target. For each sample, the filter sequence 28, 21, 23, 25 is used and the reading at $\lambda_o$ of filter 23, corrected for both background photoluminescence and any drift of detector 51 since standardization.

It should be noted that while the reference ruby fluorescence is present during each sequence of pulses measuring output at $\lambda_-$, $\lambda_o$ and $\lambda_+$, the ruby fluorescence wavelength is well outside the acceptance bandwidth of filters at these wavelengths, which for terbium chelates are at about 5300 A°, 5475 A° and 5650 A°, respectively. It should also be pointed out that during the reference measurement of ruby fluorescence of ruby 39, there may be present a small amount of photoluminescent background at the ruby wavelength, $\lambda_R$. This effect may be minimized by utilizing the fact that the ruby signal is in general very much stronger than background signals at $\lambda_R$. We can thus choose an interference filter 28 with extremely narrow bandwidth and furthermore add sufficient attenuation to the filter in the region of $\lambda_R$ to attenuate substantially all of the photoluminescent background at $\lambda_R$ but allow a sufficient amount of ruby fluorescence through to enable calibration.

Figure 3A:
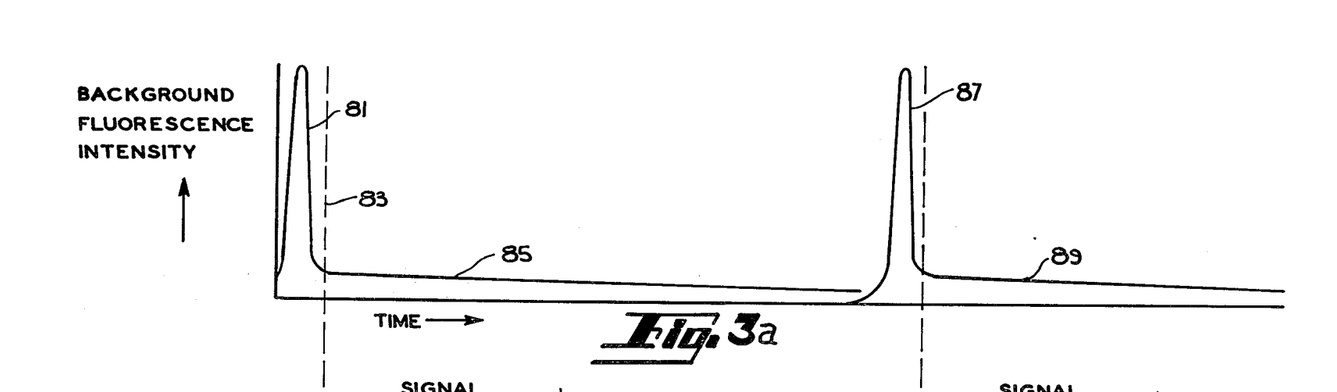
FIGS. 3a and 3b show a background signal, and a long lived tag signal as functions of time and identify different measuring periods for a pulsed system.

FIG. 3a shows a graph of background fluorescence intensity with respect to time. In FIG. 3a, a laser excitation pulse, not shown, has a very sharp cutoff which excites both background and target photoluminescence.

Most of the background substances have short decay lifetimes, the longest of which usually decays prior to 0.5 milliseconds. The curve 81 shows this background characteristic wherein the level of background fluorescence intensity rises rapidly and peaks and then rapidly falls. The dashed line 83 indicates that at 0.5 milliseconds, substantially all of the "prompt" fluorescence intensity has decayed and only a small amount of "delayed" fluorescence and phosphorescence represented by the tail 85 of the background remains. The excitation pulse starts at zero and typically has a very sharp cutoff. Excitation pulses may have a duration in the range of 1 nanosecond or shorter to a few microseconds or longer. In the former case "prompt" background duration is about 50 nanoseconds long while in the latter case background will last slightly longer than the excitation pulse. In pulsed operation, the fluorometer of the present invention repeats excitation pulses every 10 milliseconds and stores and integrates photocurrent signals for many pulses. A second photoluminescent background pulse represented by the curve 87 which rapidly decays into a tail 89 representing delayed fluorescence and phosphorescence, is shown in FIG. 3a.

Figure 3B:
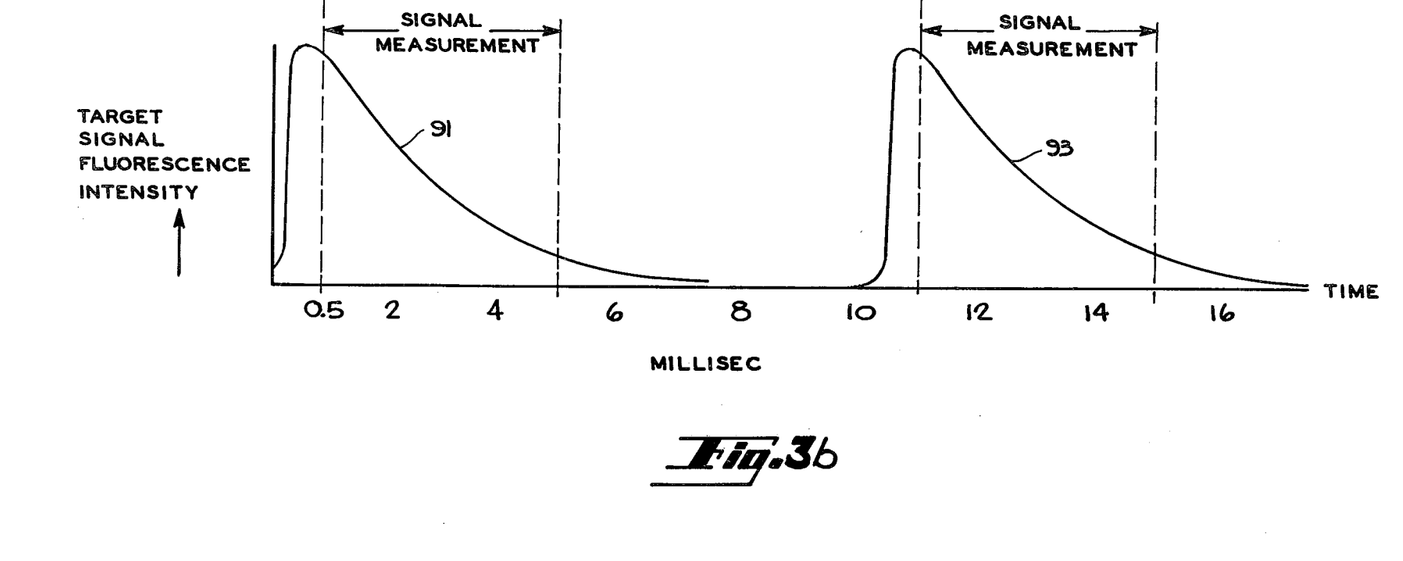

In FIG. 3b the target signal fluorescence intensity is shown for a rare earth target, such as terbium. It will be seen that terbium has a very long lifetime compared to most background, i.e. the prompt background. This background can be eliminated by gating the detection system on after the prompt or short lived background has decayed, but while the long lived signal of the target fluorophore is still above zero. The long lived background, represented by the tail 85 in FIG. 3a, together with the fluorescent decay of the target, is measured in the photodetector which is on from say 0.5 milliseconds to approximately 5.5 milliseconds. During this interval the long lived fluorescence decay of the target fluorophore is separated from the background delayed fluorescence and phosphorescence by using the interference filters 21, 23, 25, 28 in the fluorometer system of FIG. 2. The measurement is repeated beginning at 10 milliseconds when another excitation pulse excites background, together with the target substance. After approximately 0.5 milliseconds, substantially all of the short lived background has decayed and at that time the detector system is gated on and the long lived decay of the target, represented by the curve 93, is measured and separated from delayed fluorescence and phosphorescence of background represented by tail 89 in FIG. 3a, by means of the interference filters in the fluorometer system of FIG. 2.

In operation, measurements are first made of ruby fluorescence using the ruby 39, the light pipe 26, and the ruby filter 28. Next, a series of target measurements is made using each of the filters 21, 23, 25 for subtracting background from the signal representing target plus background. In each instance, the detector system is gated on after the short lived background fluorescence has decayed.

It may also be desirable to monitor dark current and stray continuous light during the time interval from 9 msec to 10 msec just before the next laser pulse. Dark current and stray light current drift would then be a further correction which could then be applied by the signal processor.

In the above method, we have ignored inner filter effects. These effects are due to attenuation in the sample at the excitation and luminescent wavelengths. A discussion of these effects appears in "Photoluminescence in Solutions" by Parker mentioned above.

These effects result in a decrease in luminescence at the detector for a given amount of target. In the case of samples that exhibit this effect, the standardization curves may be taken in a medium identical with the target medium and the effects are automatically accounted for. That is if the standardized medium exhibits the same inner filter effects as the sample medium the calibration curve automatically accounts for these effects. However, with the procedure outlined above, care must be taken that any added reagents should not change the inner filter effects.

Should it become necessary to use samples which have inner filter effects and where an identical medium is unavailable during standardization procedure, this can be handled by monitoring the attenuation in the regions of excitation and emission wavelengths for the sample medium, using the ratio of the readings at detectors 61 and 63. Additional corrections would then need to be applied to the sample readings. In the case of the correction for the excitation wavelength attenuation, this factor has been calculated by Parker and corresponds to calculating the average intensity of excitation as it traverses the sample, and computing the factor to multiply the observed fluorescence to arrive at the value that the target fluorescence would have in the absence of the attenuation. A similar calculation for attenuation of fluorescence as it travels out of the sample depends upon the geometry of the excitation beam and collecting optics, and is a straightforward integration. The method of the present invention can compensate for differences in background of the sample medium and standardization medium which result from a change in the background photoluminescence due to various reagents used in target preparation and which may not be present in standardization samples.

What is claimed is:

1. A method of photoluminescent background correction in the detection of a photoluminescent target substance admidst photoluminescent ambient substances comprising, selecting a photoluminescent target substance from the group consisting of fluorophores and substances labelled with fluorophores, said fluorophores having a sharp photoluminescent emission spectrum in comparison with the combined broad emission spectrum of ambient substances, sampling and measuring an amount of photoluminescence in a first selected narrow wavelength band centered at the peak of the principal emission wavelength of the selected target substance, said amount of photoluminescence composed of both target and ambient photoluminescence, said photoluminescence derived from an amount of excitation energy, sampling and measuring an amount of ambient photoluminescence in at least one other narrow wavelength band proximate to but substantially outside of said first selected band, said photoluminescence derived from said amount of excitation energy, converting said measured amount of ambient photoluminescence in the other selected wavelength bands into an amount which would occur from ambient photoluminescence measured in said first selected wavelength band, and subtracting said converted amount from the measured amount due to both target and ambient substances.

2. The method of claim 1 wherein ambient photoluminescence is sampled and measured in two selected wavelength bands, one on each side of the principal target emission band, but substantially outside of said band.

3. The method of claim 1 further defined by selecting said photoluminescent target to have a photoluminescent decay lifetime long compared with the longest of the fluorescent decay lifetimes of ambient surfaces for time domain discrimination against ambient fluorescence.

4. The method of claim 1 wherein said fluorophore is a fluorescent rate earth chelate.

5. The method of claim 1 further defined by stabilizing the amount of excitation energy used in each measuring process.

6. The method of claim 5 further defined by measuring the photoluminescence of an internal standard excited with a fixed amount of excitation energy at defined time intervals and compensating measured amounts of target and ambient photoluminescence for deviations due to drift.

7. A spectrofluorometer for detecting targets having a sharp photoluminescent emission spectrum in comparison with the combined broad emission spectrum of ambient substances comprising, an excitation beam source, means for supporting a photoluminescent target in said excitation beam, means for sampling and measuring an amount of photoluminescence from said target and ambient substances present in the target area in preselected bandwidths, said sampling and measuring means having a photodetector and a wavelength band selector capable of selecting a narrow first wavelength band at the peak of the principal emission wavelength of the target substance and in at least one other narrow wavelength band proximate to, but substantially outside of said first wavelength band, and signal processing means for converting said measured amount of ambient photoluminescence in the proximate selected wavelength bands into an amount which would occur from the ambient photoluminescence measured in said first selected wavelength band and subtracting said converted amount from the measured amount due to both target and ambient substances.

* * * * *

UNITED STATES PATENT AND TRADEMARK OFFICE
CERTIFICATE OF CORRECTION

PATENT NO. : 4,150,295

DATED : April 17, 1979

INVENTOR(S) : Irwin Wieder, Los Altos, California

It is certified that error appears in the above-identified patent and that said Letters Patent are hereby corrected as shown below:

Column 7, line 54, the term "$\lambda_{31}$" should read --$\lambda_-$--;

Claim 3, Column 11, line 13, the term "surfaces" should read --substances--;

Claim 4, Column 11, line 17, the term "rate" should read --rare-

Signed and Sealed this

Fourteenth Day of August 1979

[SEAL]

Attest:

Attesting Officer

LUTRELLE F. PARKER
Acting Commissioner of Patents and Trademarks